United States Patent [19]
Nelson et al.

[11] Patent Number: 6,102,880
[45] Date of Patent: Aug. 15, 2000

[54] WRIST BRACE

[75] Inventors: Ronald E. Nelson, Cambridge, Minn.; Herbert M. Raschka, Sauk City, Wis.

[73] Assignee: Mueller Sports Medicine, Inc., Prairie du Sac, Wis.

[21] Appl. No.: 09/408,901

[22] Filed: Sep. 29, 1999

[51] Int. Cl.[7] ........................................................ A61F 5/00
[52] U.S. Cl. .................................. 602/21; 602/5; 602/20; 602/60; 602/64
[58] Field of Search .......................... 2/160, 161.1, 161.2, 2/161.3, 161.4–161.7, 159, 162; 128/878–880, 877; 473/61, 62, 63; 482/44, 45, 46; 602/5, 20, 21, 22, 60, 61, 62, 64

[56] References Cited

U.S. PATENT DOCUMENTS

| | | |
|---|---|---|
| 5,205,812 | 4/1993 | Wasserman . |
| 5,265,445 | 11/1993 | Shytles et al. . |
| 5,267,943 | 12/1993 | Dancyger . |
| 5,345,368 | 9/1994 | Huff . |
| 5,409,451 | 4/1995 | Daneman . |
| 5,520,621 | 5/1996 | Edenbaum et al. . |
| 5,522,241 | 6/1996 | King . |
| 5,672,150 | 9/1997 | Cox . |
| 5,713,837 | 2/1998 | Grim et al. . |
| 5,725,490 | 3/1998 | Conran . |
| 5,728,059 | 3/1998 | Wiesemann et al. . |
| 5,746,707 | 5/1998 | Eck . |
| 5,759,166 | 6/1998 | Nelson et al. . |
| 5,766,141 | 6/1998 | Gould . |
| 5,769,804 | 6/1998 | Harris et al. . |
| 5,772,620 | 6/1998 | Szlema et al. . |
| 5,868,692 | 2/1999 | Michniewicz . |

*Primary Examiner*—Kim M. Lee
*Attorney, Agent, or Firm*—Lathrop & Clark LLP

[57] ABSTRACT

A lightweight wrist brace has a flexible base which extends along the palm and receives a stiffening member within a pocket. A narrow hand strap extends upwardly and sidewardly from the base at about 105–120 degrees on each side of the base. The two hand straps wrap around the hand and are connected to each other with hook and loop fasteners across the dorsal area of the hand. Two wrist straps are spaced from one another at the rearward end of the base. The wrist straps have hook material and loop material disposed thereon and are releasably received within rings positioned adjacent each strap where it extends from the base. The wrist brace is thus capable of being worn on either a right or a left hand and is adapted for wear by people with varying size wrist and hands.

27 Claims, 3 Drawing Sheets

WRIST BRACE

BACKGROUND OF THE INVENTION

The present invention relates to appliances for restricting human joint movement in general, and to devices for controlling movement of the wrist in particular.

Industrial and post-industrial economies have placed emphasis on the efficient performance of specialized tasks. In many fields, this specialization leads to the repetition of similar physical actions dozens or hundreds of times a day. These repeated small tasks can result in injuries which have been grouped together under the heading of Cumulative Repetitive Stress Syndromes (CRSS) or Repetitive Strain Injury (RSI). Particular maladies affecting the wrist include Carpal Tunnel Syndrome and tendinitis. One approach to lessening the pain associated with repetitive wrist movements is to restrain the wrist to prevent the motions which lead to discomfort.

Many wrist braces have been developed to address this need. Some designs are specially configured for the left or the right hand and come in a range of sizes. Where a wrist brace is custom built for a particular patient, the wide range of shapes and sizes is not a concern. However, where the brace is intended for retail sale, providing different braces for left and right wrists demands a doubling of the number of items which must be kept on hand by the retailer. The multiplicity of products, or stock keeping units, is increased proportionately when braces in small, medium, large, or other sizes are also required for each hand. U.S. Pat. No. 5,759,166 to Nelson discloses a wrist brace having a stretchable fabric base which encircles the wrist and is clasped in position by straps and hook and loop fasteners. This unit, although made in various sizes, may be worn on either the left or right hand.

A single wrist brace which is suitable for either hand and hands of various sizes, would greatly reduce the inventory required by a particular retailer and would permit other product options such as color to be manageable. In addition, a brace which would perform the necessary motion restricting function with minimal material and minimal discomfort to the wearer would lessen the reluctance of a repetitive strain injury sufferer to make use of the brace.

SUMMARY OF THE INVENTION

The wrist brace of this invention has a flexible base formed of two layers which define a pocket therebetween. The layer which extends adjacent the wearer's skin is preferably formed of ventilated elastic material. The base extends along the palmer side of the hand and receives a bent metal stiffening member within the pocket. A hand strap extends upwardly and sidewardly from the base on each side of the stiffening member. The narrow hand straps extend from the base at an angle of greater than 90 degrees, approximately 105–120 degrees. The hand straps are positioned forward of the base of the thumb and rearwardly of the knuckles. Hook fabric is positioned on one face of one of the hand straps, while loop fabric is positioned on the opposite face of the other hand strap. The two hand straps wrap around the hand and are connected to each other across the dorsal area of the hand. Two wrist straps are spaced from one another at the rearward end of the base. The wrist straps have hook material and loop material disposed thereon and are releasably received within rings positioned adjacent each strap where it extends from the base. The wrist brace is thus capable of being worn on either a right or a left hand and is adapted for wear by people with varying size wrist and hands. In addition, the light weight and open construction of the wrist brace minimizes discomfort during wear.

It is an object of the present invention to provide a wrist brace which is light weight and which does not fully enclose the palm.

It is another object of the present invention to provide a wrist brace which may be worn on either the right hand or the left hand, and which is wearable by users of a range of sizes.

It is a further object of the present invention to provide a wrist brace which gives complete freedom of motion to the wearer's fingers.

It is also an object of the present invention to provide a wrist brace with minimal surface contact with the wearer's hand to promote air flow past and cooling of the hand.

Further objects, features and advantages of the invention will be apparent from the following detailed description when taken in conjunction with the accompanying drawings.

DESCRIPTION OF THE PREFERRED EMBODIMENTS

Figures 1, 2:
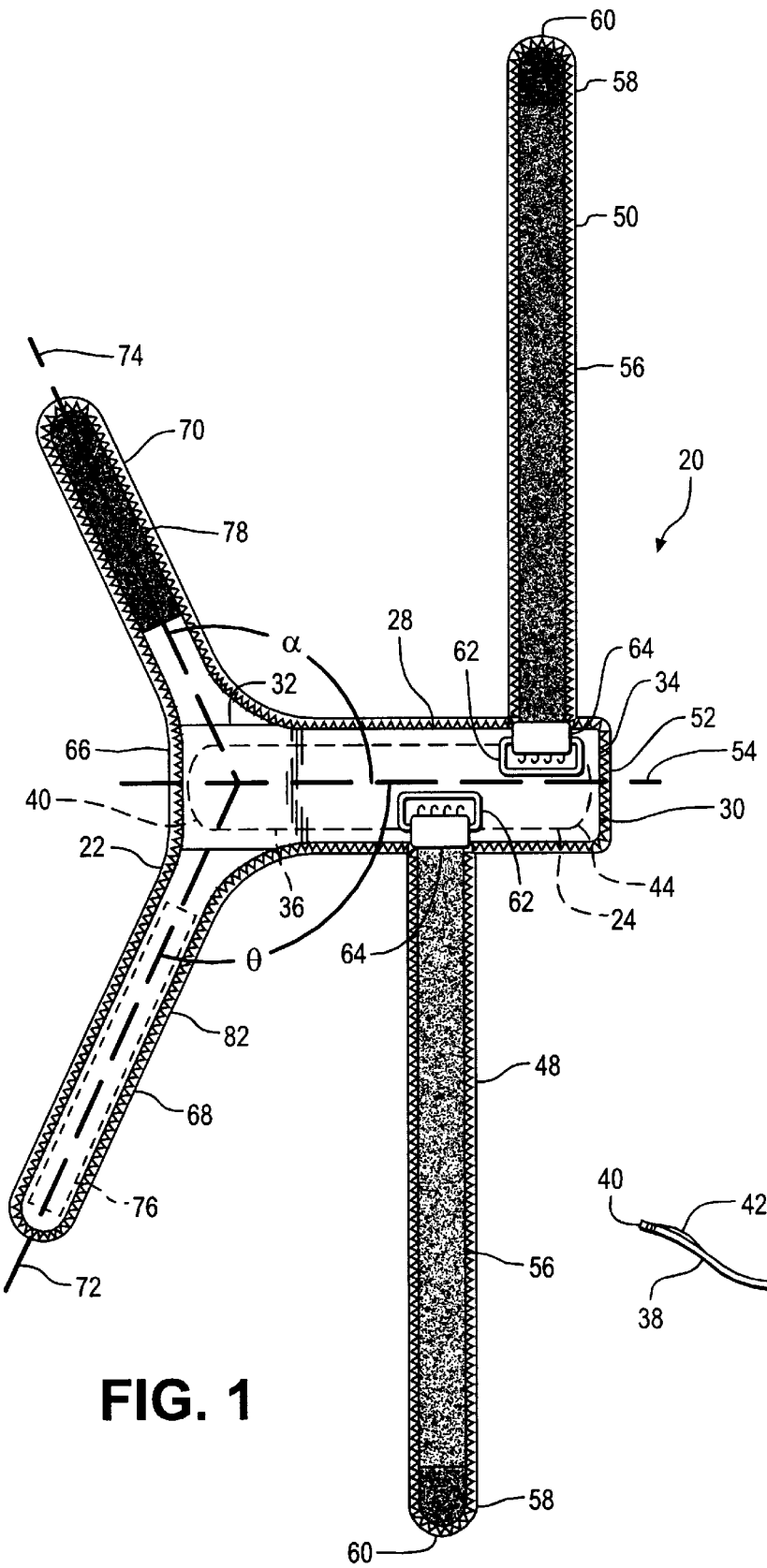
FIG. 1 is a bottom plan view of the wrist brace of this invention.
FIG. 2 is a side elevational view of the support spoon or stiffening member of the wrist brace of FIG. 1.

Referring more particularly to FIGS. 1–5, wherein like numbers refer to similar parts, the wrist brace 20 of this invention is shown in FIG. 1. The wrist brace 20 has a flexible body 22 which receives a rigid spoon or stiffening member 24. The wrist brace 20 has four straps which permit it to be releasably attached to the hand 26 of a wearer. The body 22 of the wrist brace 20 has a base member 28 which extends across the wrist joint and onto the palm of the wearer. The base member is comprised of a first panel 30 which faces outwardly, away from the wearer's palm, and a second panel 32 is positioned above the first panel. The first panel 30 is preferably formed of vinyl or leather material, or other material which has good wear and cleanability characteristics. A smooth impervious surface for the first panel 30 is also desirable to avoid catching or tearing as the wearer grips and carries item. The second panel 32 is preferably formed of a stretchable and breathable material such as ventilated elastic, such as the material disclosed in U.S. Pat. Nos. 5,265,445 or 5,522,241, the disclosures of which are incorporated by reference herein. The vapor permeable panel advantageously allows liquid, such as sweat, to move away from contact with the wearer's skin, minimizing dampness.

Figure 5:
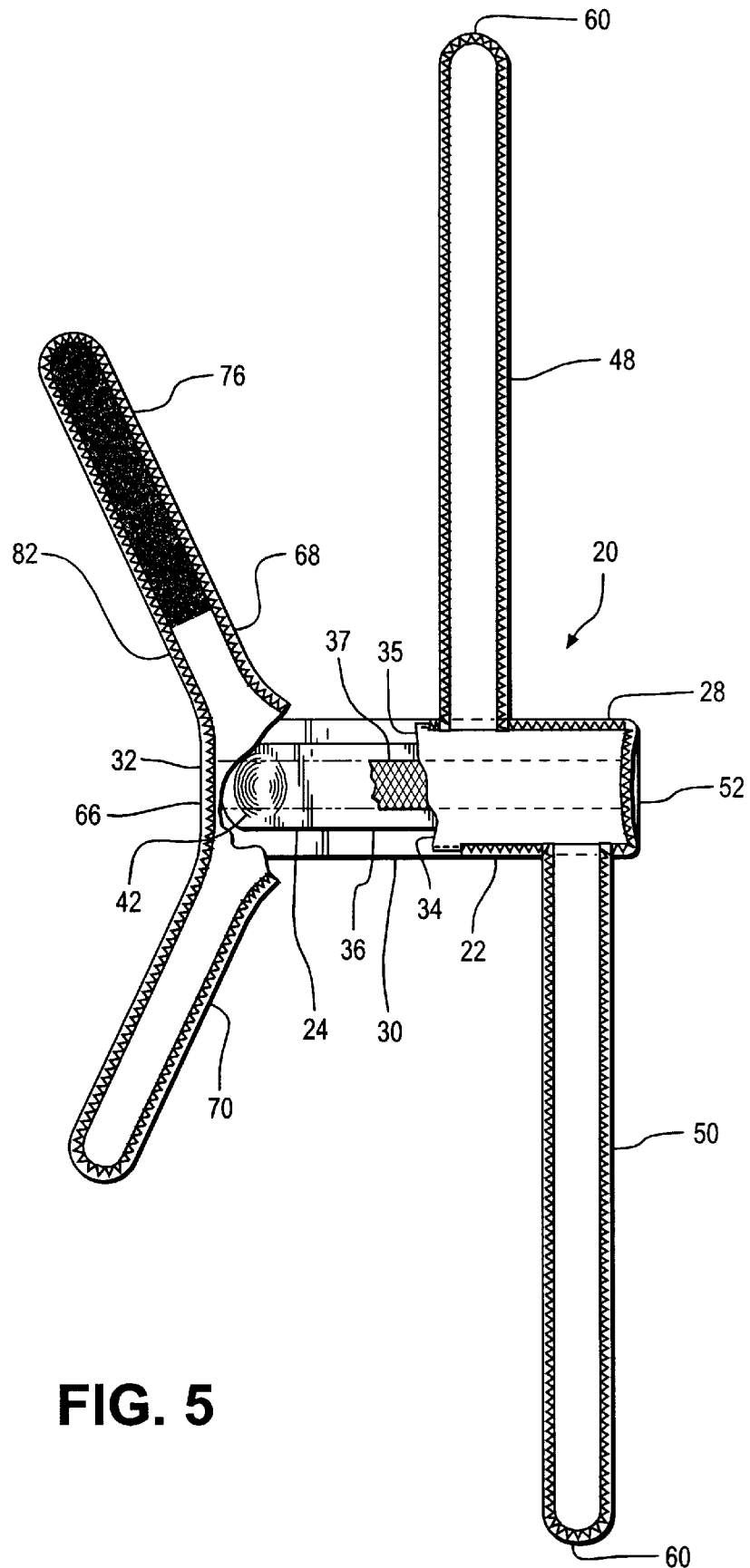
FIG. 5 is a top plan view of the wrist brace of FIG. 1, partially cut away in section to reveal the interior structure thereof.

The first panel 30 is stitched or otherwise connected to the second panel 32 to define an axially extending pocket 34 running the length of the base member 28. The pocket 34 receives the stiffening member 24. As shown in FIG. 5, a rectangular third panel 35 of ⅛th inch foam rubber, with a soft fabric finish, is sewn to the top side of the second panel 32. The third panel 35, which engages the skin of the wearer, is non-abrasive and plush, to provide comfortable contact. A relatively non-stretchable woven cotton ribbon 37 is sewn to the underside of the second panel 32 and overlies the stiffening member 24.

As shown in FIG. 2, the stiffening member 24 may be formed of stiff plastic, but is preferably a stamped metal part, for example aluminum approximately 1/16 inches thick. The stiffening member 24 has a flat central section 36 which extends upwardly to define a palm section 38 which has a curved forward end 40. A semispherical projection 42 extends upwardly from the palm section 38. A curved rearward end 44 extends downwardly from the central section 36 at the end opposite the forward end 40. The rearward end 44 of the stiffening member 24 is positioned by the pocket 34 to underlie the wearer's arm. The downward extension of the rearward end 44 minimizes contact between the protruding end of the stiffening member and the wearer's arm, promoting comfortable wearing of the brace 20.

The stiffening member is about 6 inches long from end to end, with the palm section extending about one inch, and the rear end extending about 1/4 inch. The pocket 34 is preferably closed on the sides and the front by stitching, and is open at the rear to permit removal of the stiffening member 24 as desired, for example when the body of the brace is to be cleaned.

The brace 20 is connected between the wearer's hand 26 and forearm 46 to bridge the wrist 47 and restrict the extension and flexion of the wrist. The brace is attached to the wearer's forearm 46 by a first wrist strap 48 and a second wrist strap 50. The second wrist strap 50 is positioned adjacent the rear end 52 of the base member 28 on one side of an imaginary line 54 defining the central axis of the base member 28. The first wrist strap 48 is spaced toward the palm from the second wrist strap 50 and is attached to the base member 28 across the central axis 54 from the second wrist strap. As best shown in FIG. 1, each wrist strap 48, 50 is approximately ten inches long and about one inch wide and has a downwardly facing segment of loop material 56 which extends from the base member to a shorter segment of hook material 58 adjacent the free end 60 of each wrist strap. The loop material segment 56 and the hook material segment 58 may be brought together to serve as a hook and loop fastener. A square metal ring 62 is sewn to the base member 28 by a loop of material 64 adjacent the base of each wrist strap 48, 50.

To fasten the brace 20 to the wearer's forearm 46, the free end 60 of both wrist straps are passed around the forearm, then each strap is passed through its corresponding ring 62 and then folded back onto itself and tightened to the desired degree. The first wrist strap 48 is preferably wrapped directly around the wrist joint itself, while the second wrist strap 50 is positioned rearwardly of the wrist joint at a location on the wearer's forearm.

The forward end 66 of the base member 28 is fastened to the wearer's hand by two hand straps 68, 70 which extend upwardly from the base member. The first hand strap 68 extends from the base member on the same side as the first wrist strap 48. The second hand strap 70 extends from the base member 28 on the same side as the second wrist strap 50. As shown in FIG. 1, the hand straps 68, 70 are preferably formed from the same sheet of material which defines the second panel 32. The first hand strap 68 extends about 5½ inches from the base member 28, and the second hand strap extends about 4½ inches from the base member. Each hand strap 68, 70 is about one inch wide. Each hand strap 68, 70 may be imagined to have a strap axis 72, 74 which intersects the base member central axis 54. The first hand strap axis 72 defines an angle θ with the base member central axis, while the second hand strap axis 74 defines an angle α with the base member central axis. Both hand straps extends from the base member at an angle which is greater than 90 degrees, and preferably about 105–120 degrees, for example 110 degrees. It should be noted that the ventilated elastic material from which the base member and the hand straps are formed has an axis of preferential extension, that is, a direction in which the material is particularly stretchable. The axis of preferential extension runs approximately perpendicular to the base member central axis 54. Because the hand straps 68, 70 extend at other than a perpendicular angle to the central axis, it will be noted that the axes of preferential extension on the hand straps do not align with the hand strap axes 72, 74, although the direction of preferential extension is still such that the material of the hand straps is more stretchable as it extends around the hand, than it is in a direction from the front to the rear of the hand.

The first hand strap 68 has a segment of loop material 76 positioned at the free end on the side of the first strap opposite the side of the base member to which the first panel 30 is connected. The second hand strap 70 has a segment of hook material 78 which is on the same side of the base member to which the first panel 30 is connected.

Figure 3:
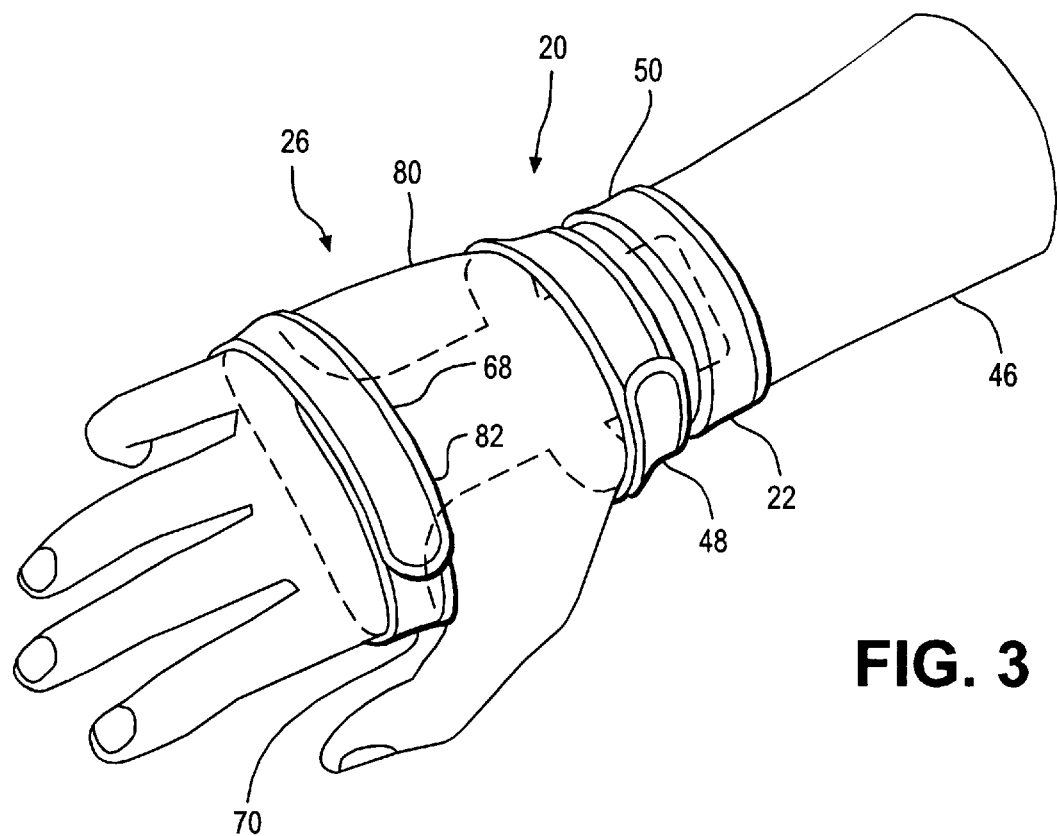
FIG. 3 is a top perspective view of the wrist brace of FIG. 1 positioned on a wearer's right hand and wrist.
Figure 4:
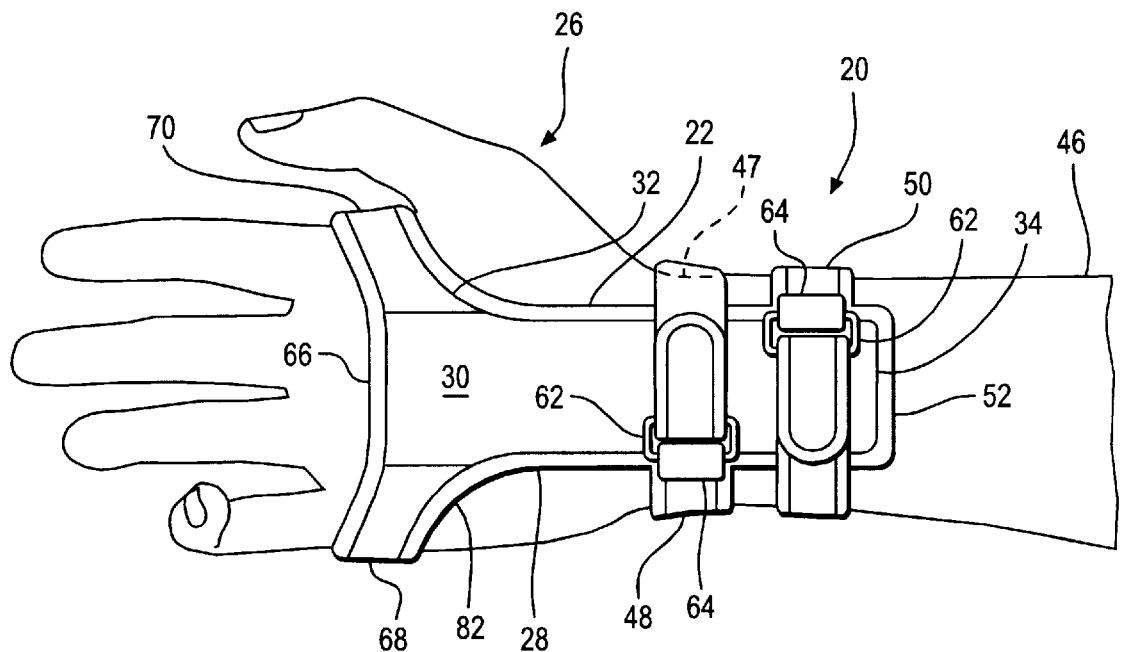
FIG. 4 is a bottom perspective view of the wrist brace of FIG. 3 positioned on a wearer's right hand and wrist.

As shown in FIG. 4, the brace is attached to the wearer's hand 26 by passing both the first strap 68 and the second strap 70 over the palm and around to the dorsal side 80 of the hand where the straps are overlapped behind the knuckles. The overlapped hand straps 68, 70 are then connected to one another by the engagement of the hook material 78 with the loop material 76. As shown in FIG. 3, one of the hand straps wraps around the hand rearwardly of the little finger first joint, while the other hand strap wraps around the hand between the base of the thumb and the first joint of the first finger.

To prevent the fraying of the edges of the ventilated elastic material, a narrow strip of cotton polyester binding 82 is sewn around all exposed edges.

Several beneficial features of this construction should be noted. First, the brace 20 may equally be applied to a left hand or a right hand. Second, because of its attachment to the hand behind the knuckle, the brace has minimal interference with the free movement of the wearer's fingers. This is particularly advantageous for wearers who are engaged in tasks requiring manual dexterity such as keyboard operations, needlework, assembly, and other types of hand work. Third, because the hand straps are connected to one another, and not to some sleeve or fabric member further back on the wrist, the brace 20 leaves the back of the hand substantially unobstructed, thereby promoting air flow and cooling across the hand. In addition, because the brace 20 is constructed of minimal material, it is of lower weight, and thus less distracting to the wearer. Moreover, fewer materials contribute to a more economically produced product.

Because the hand and wrist straps may be made large enough to accommodate a wide range of palm and wrist circumferences with minimal weight penalty, and because most variations in hand size are experienced as differences in finger length, wrist circumference, and palm circumference, the brace 20 may be produced in a single size which will accommodate a wide range of wearers. A few sizes will accommodate all possible wearers. The ability of one or a few sizes of brace to accommodate all customers makes possible a variety of brace options which could not be supported if each option had to be supplied in a half-dozen or more sizes. For example, braces may be supplied in different price ranges, ranging from a low-cost plastic model to a more expensive leather or fabric model. Alternatively, braces may be supplied in a variety of patterns or colors to suit the fashion preferences of the user.

It is understood that the invention is not limited to the particular construction and arrangement of parts herein illustrated and described, but embraces such modified forms thereof as come within the scope of the following claims.

I claim:

1. A wrist brace comprising:

a base member extending along a first front to back axis;

a stiffening member;

portions of the base member which receive the stiffening member, attaching the stiffening member to the base member to extend from the wrist to the palm of a wearer during use;

at least one wrist strip extending from the rear of the base member, and of sufficient length to wrap around the wearer's wrist and attach to the base member;

a first hand strap which extends from the base member at an angle to the first axis of greater than 90 degrees; and a second hand strap which extends from the base member at a position opposite the first hand strap at an angle to the first axis of greater than 90 degrees, wherein a hook material is positioned on one face of one of the hand straps and a loop material is positioned on an opposite face of the other of the hand straps, such that the two hand straps are wrapable about the wearer's hand forward of the base of the thumb and rearward of the knuckles and attachable to one another such that the hook material on one hand strap engages the loop material on the other hand strap.

2. The wrist brace of claim 1 wherein the at least one wrist strap comprises:

a first wrist strap; and a second wrist strap spaced frontwardly from the first wrist strap.

3. The wrist brace of claim 1 wherein the first hand strap and the second hand strap each extend from the base member at an angle to the first axis of between 105 and 120 degrees.

4. The wrist brace of claim 1 wherein the base member comprises a first panel connected to a second panel to define a rearwardly opening pocket which receives the stiffening member therein.

5. The wrist brace of claim 1 further comprising a foam panel connected to the base member to face the wearer's palm.

6. The wrist brace of claim 1 wherein the base member comprises a sheet of ventilated elastic material, and wherein the first hand strap and the second hand strap are formed as a part of said sheet.

7. The wrist brace of claim 1 wherein the base member, the at least one wrist strap, and the hand straps have exposed edges, and wherein a narrow strip binding is sewn around all said exposed edges.

8. The wrist brace of claim 1 wherein the stiffening member has a central section with an upwardly extending front section and a downwardly extending rear section.

9. The wrist brace of claim 1 wherein a ring is fastened to the base member opposite the first wrist strap, and wherein the first wrist strap has an end portion on a first surface from which one half of a hook and loop fastener projects, and a portion of the first wrist strap on the first surface adjacent the end portion has another half of a hook and loop fastener, such that the first wrist strap is extendable through the ring and foldable back upon itself to be adjustably fastened around a wearer's wrist.

10. A wrist brace comprising:

a base member which extends from front to back;

a stiffening member;

portions of the base member which receive the stiffening member, attaching the stiffening member to the base member to extend from the wrist to the palm of a wearer;

at least one wrist strap extending sidewardly from the rear of the base member, the wrist strap being flexible to permit its being wrapped around the wrist of a user and connected to the base member;

a first hand strap which extends sidewardly from the base member; and a second hand strap which extends sidewardly from the base member at a position opposite the first hand strap, wherein portions of the first hand strap and the second hand strap cooperate to permit the first hand strap and the second hand strap to be engaged with and connected to one another at a position on the dorsal side of the hand, such that the two hand straps are wraped about the wearer's hand forward of the base of the thumb and rearward of the knuckles.

11. The wrist brace of claim 10 wherein the at least one wrist strap comprises:

a first wrist strap; and a second wrist strap connected to the base member and spaced frontwardly from the first wrist strap.

12. The wrist brace of claim 10 wherein the first hand strap and the second hand strap each extend from the base member at an angle to the base member of between 105 and 120 degrees.

13. The wrist brace of claim 10 herein the base member comprises a first panel connected to a second panel to define a rearwardly opening pocket which receives the stiffening member therein.

14. The wrist brace of claim 10 wherein the stiffening member has a central section with an upwardly extending front section and a downwardly extending rear section.

15. The wrist brace of claim 10 further comprising a foam panel connected to the base member to face the wearer's palm.

16. The wrist brace of claim 10 wherein the base member comprises a sheet of ventilated elastic material, and wherein the first hand strap and the second hand strap are formed as a part of said sheet.

17. The wrist brace of claim 10 wherein the base member, the at least one wrist strap, and the hand straps have exposed edges, and wherein a narrow strip binding is sewn around all said exposed edges.

18. The wrist brace of claim 10 wherein a ring is fastened to the base member opposite the first wrist strap, and wherein the first wrist strap has an end portion on a first surface from which one half of a hook and loop fastener projects, and a portion of the first wrist strap on the first surface adjacent the end portion has another half of a hook and loop fastener, such that the first wrist strap is extendable through the ring and foldable back upon itself to be adjustably fastened around a wearer's wrist.

19. A wrist brace comprising:

a base member which extends from front to back;

a stiffening member;

portions of the base member which receive the stiffening member, attaching the stiffening member to the base member to extend from the wrist to the palm of a wearer;

at least one wrist strap extending sidewardly from the rear of the base member, the wrist strap being flexible to permit its being wrapped around the wrist of a user and connected to the base member;

a first hand strap which extends sidewardly from the base member; and a second hand strap which extends sidewardly from the base member at a position opposite the first hand strap, wherein portions of the first hand strap and the second hand strap cooperate to permit the first hand strap and the second hand strap to be engaged with and connected to one another at a position on the dorsal side of the hand, such that the two hand straps are wrapped about the wearer's hand forward of the base of the thumb and rearward of the knuckles.

20. The wrist brace of claim 19 wherein the at least one wrist strap comprises:

a first wrist strap; and a second wrist strap connected to the base member and spaced frontwardly from the first wrist strap.

21. The wrist brace of claim 19 wherein the first hand strap and the second hand strap each extend from the base member at an angle to the base member of between 105 and 120 degrees.

22. The wrist brace of claim 19 wherein the base member comprises a first panel connected to a second panel to define a rearwardly opening pocket which receives the stiffening member therein.

23. The wrist brace of claim 19 wherein the stiffening member has a central section with an upwardly extending front section and a downwardly extending rear section.

24. The wrist brace of claim 19 wherein a ring is fastened to the base member opposite the first wrist strap, and wherein the first wrist strap has an end portion on a first surface from which one half of a hook and loop fastener projects, and a portion of the first wrist strap on the first surface adjacent the end portion has another half of a hook and loop fastener, such that the first wrist strap is extendable through the ring and foldable back upon itself to be adjustably fastened around a wearer's wrist.

25. The wrist brace of claim 19 further comprising a foam panel connected to the base member to face the wearer's palm.

26. The wrist brace of claim 19 wherein the base member comprises a sheet of ventilated elastic material, and wherein the first hand strap and the second hand strap are formed as a part of said sheet.

27. The wrist brace of claim 19 wherein the base member, the at least one wrist strap, and the hand straps have exposed edges, and wherein a narrow strip binding is sewn around all said exposed edges.

* * * * *